(12) United States Patent
Pritchard et al.

(10) Patent No.: US 11,510,978 B2
(45) Date of Patent: Nov. 29, 2022

(54) MODIFIED MAREK'S DISEASE VIRUS, AND VACCINES MADE THEREFROM

(71) Applicant: Boehringer Ingelheim Animal Health USA Inc., Duluth, GA (US)

(72) Inventors: Joyce Pritchard, Gainesville, GA (US); Teshome Mebatsion, Watkinsville, GA (US); Michel Bublot, Chaponost (FR)

(73) Assignee: Boehringer Ingelheim Animal Health USA Inc., Duluth, GA (US)

( * ) Notice: Subject to any disclaimer, the term of this patent is extended or adjusted under 35 U.S.C. 154(b) by 0 days.

(21) Appl. No.: 16/262,774

(22) Filed: Jan. 30, 2019

(65) Prior Publication Data

US 2019/0216920 A1 Jul. 18, 2019

Related U.S. Application Data

(63) Continuation of application No. 13/841,684, filed on Mar. 15, 2013, now abandoned.

(60) Provisional application No. 61/614,142, filed on Mar. 22, 2012.

(51) Int. Cl.
*A61K 39/255* (2006.01)
*A61K 39/12* (2006.01)
*A61K 39/00* (2006.01)

(52) U.S. Cl.
CPC .......... *A61K 39/255* (2013.01); *A61K 39/12* (2013.01); *A61K 2039/5254* (2013.01); *A61K 2039/552* (2013.01); *C12N 2710/16334* (2013.01); *C12N 2740/13022* (2013.01); *C12N 2830/60* (2013.01)

(58) Field of Classification Search
None
See application file for complete search history.

(56) References Cited

U.S. PATENT DOCUMENTS

2005/0019348 A1* 1/2005 Reddy .................. A61K 39/255
424/199.1

FOREIGN PATENT DOCUMENTS

EP 2827898 12/2017

OTHER PUBLICATIONS

Witter, R. L., et al. "Retroviral insertional mutagenesis of a herpesvirus: a Marek's disease virus mutant attenuated for oncogenicity but not for immunosuppression or in vivo replication." Avian diseases (1997): 407-421.
Jones, Dan, et al. "Retroviral insertional activation in a herpesvirus: transcriptional activation of US genes by an integrated long terminal repeat in a Marek's disease virus clone." Journal of virology 70, No. 4 (1996): 2460-2467.
Jones, Dan, et al., "Retroviral insertions into a herpesvirus are clustered at the junctions of the short repeat and short unique sequences." Proceedings of the National Academy of Sciences 90, No. 9 (1993): 3855-3859.
Kost, Rhonda, et al. "Retrovirus insertion into herpesvirus: characterization of a Marek's disease virus harboring a solo LTR." Virology 192, No. 1 (1993): 161-169.
Isfort, Robert, et al. "Retrovirus insertion into herpesvirus in vitro and in vivo." Proceedings of the National Academy of Sciences 89, No. 3 (1992): 991-995.
Witter, R. L., et al. "Characteristics of CVI988/Rispens and R2/23, two prototype vaccine strains of serotype 1 Marek's disease virus." Avian diseases (1995): 269-284.
De Boer, G. F., et al. "Biological characteristics of Marek's disease vaccine CVI-988 clone C." Veterinary Quarterly 9, No. sup1 (1987): 16-28.

* cited by examiner

*Primary Examiner* — Nianxiang Zou
(74) *Attorney, Agent, or Firm* — Jamie L. Graham

(57) ABSTRACT

The present invention provides an effective vaccine for Marek's disease, which may be prepared using a recombinant Marek's Disease Virus (MDV), strain CVI988, having been transformed with a foreign DNA construct that includes a long terminal repeat sequence of a reticuloendotheliosis virus. This safe viral agent elicits a highly protective immune response in a chicken against virulent MDV challenge without causing a significant degree of pathogenicity. Suitable formulations of the vaccine for use in chickens include an effective immunization dosage of this novel viral agent, along with a pharmaceutically acceptable carrier or diluent.

8 Claims, 4 Drawing Sheets

Specification includes a Sequence Listing.

| Primer name | Sequence (5' 0 3') | |
|---|---|---|
| 1 | gccctgtcgaagaggaaata | SEQ ID NO:3 |
| 2 | tctcactgccaatctgagga | SEQ ID NO:4 |
| 3 | cacttgcaccatccaatcac | SEQ ID NO:5 |
| 4 | ctatttgcgcggaggaag | SEQ ID NO:6 |
| 7 | cagccttcgaaatatatctca | SEQ ID NO:7 |
| 8 | ccctttatgaaagctggcctc | SEQ ID NO:8 |
| RN1250Nco | gcgctgtccatggtaactgga | SEQ ID NO:9 |

| Primer pair | RN1250 (2 LTR) | Rispens (0 LTR) |
|---|---|---|
| 1 + 2 | 531 | - |
| 2 + 3 | 242 | - |
| 3 + 4 | 538 | - |
| 1 + 4 | 827 | 289 |
| RN1250Nco + 7 | 3510 | 2977 |
| RN1250Nco + 8 | 3762 | 3229 |

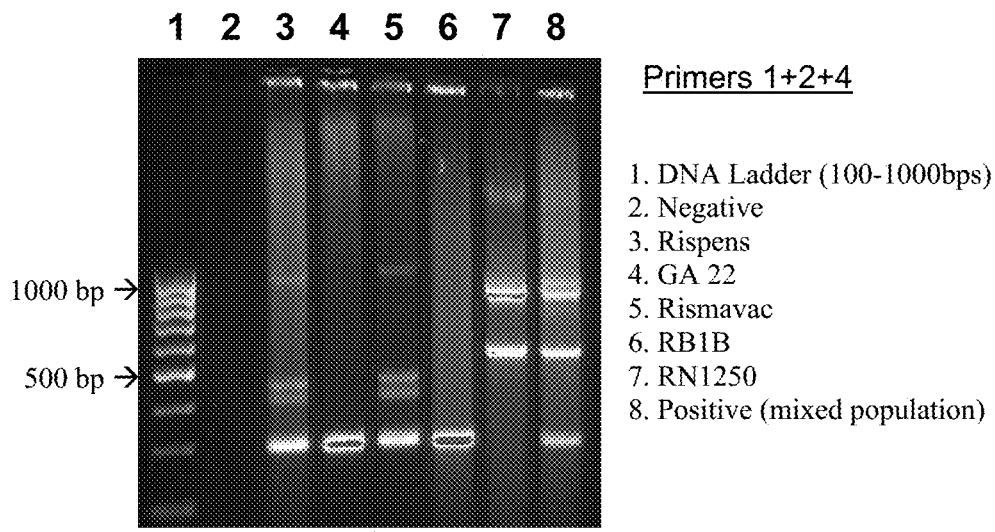

Primers 1+2+4

1. DNA Ladder (100-1000bps)
2. Negative
3. Rispens
4. GA 22
5. Rismavac
6. RB1B
7. RN1250
8. Positive (mixed population)

FIG. 3

MODIFIED MAREK'S DISEASE VIRUS, AND VACCINES MADE THEREFROM

INCORPORATION BY REFERENCE

This application claims priority to U.S. provisional patent application No. 61/614,142, which was filed on Mar. 22, 2012, and is herein incorporated by reference in its entirety.

FIELD OF THE INVENTION

The present invention relates generally to viral vaccines and methods of using the same. More particularly, the present invention relates to novel vaccines for protecting chickens against infection with Marek's disease virus, and having improved safety and efficacy over existing vaccines.

BACKGROUND

Marek's disease (MD), a highly prevalent and important lymphoproliferative disease of chickens, is controlled in commercial chickens by live virus vaccines consisting of attenuated or naturally avirulent MD-related herpesviruses. Although vaccination programs have been considered effective overall, the poultry industry continues to experience losses due to MD. Given the tendency of MD virus to become more virulent with time (e.g. by reversion to more virulent form) coupled with the economic pressures confronting the poultry industry, there remains a strong incentive to develop safer and more efficacious products that will protect better in the face of early challenge with very virulent field strains without causing adverse side effects (e.g. thymic dystrophy).

There are three distinct serotypes of MD virus found in chickens: (1) serotype 1, the oncogenic form responsible for the disease, including high- and low-virulence MD virus and their attenuated variants; (2) serotype 2, a non-oncogenic MD virus; and (3) serotype 3, herpesvirus of turkeys (HVT). An early MD vaccine consists of the serotype 3 virus originally isolated from turkeys as reported in Witter et al. [Am. J. vet. Res. 31:525-538 (1970)] and Okazaki et al. [U.S. Pat. No. 3,642,574]. Its lack of oncogenicity, self-limiting infection, good replication in vivo and in vitro, availability as cell-free and cell-associated preparations, and high protective efficacy have established HVT as a standard for WID vaccines throughout the world. A commonly used strain of HVT is FC126.

Vaccines produced from the naturally avirulent SB-1 strain [Schat et al., J. Natl. Cancer inst.60:1075-1082 (1978) and U.S. Pat. No. 4,160,024, an isolate of a serotype 2 MD virus] have been licensed in the united States since 1984. The SB-1 strain is poorly protective against the highly virulent MDV strains. It is usually used in combination with HVT as a bivalent vaccine since the two viruses together produce greater protection than does either one alone [Schat et a/., Avian Pathol. 11:593-606 (1982); Witter, Avian Pathol. 11:49-62 (1982), the contents of which are incorporated by reference herein]. This phenomenon has been termed "protective synergism." The SB-1+HVT bivalent vaccine represents greater than 50% of the United States market for MD vaccines at present and is considered to be among the most efficacious of the various MD products available. However, sporadic losses occur despite its use.

Another MD vaccine produced from strain CVI988 clone C (CVI988/C) has been licensed for commercial use in the United States. This vaccine was derived from a mildly virulent serotype 1 MD virus attenuated by serial passage in tissue culture and has been reported by De Boer et al. [Avian Dis. 30:276-283 (1986)]. A further passaged derivative of CVI988/C, identified as CVI988/C/R6, has also been described by De Boer et al. [Advances in Marek's Disease Research, pp. 405-4 3 (1988)]. More recently, the original low-passage strain, designated CVI988/Rispens, which has been in commercial use in other countries for a number of years, was found to be highly effective against challenge with several very virulent MD virus strains by Witter et al. [4th Intl. Symp. Marek's Disease, pp. 315-319 (1992)].

An experimental vaccine derived from Md11, a very virulent serotype 1 MD field isolate, was reported by Witter, supra. Md11 was attenuated by serially passaging 75 times in cell culture, and the resultant vaccine was designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

U.S. Pat. No. 4,895,717, Witter disclosed a revertant derivative of Mdn/75C which was referred to as Md11/75C/R2. Md11/75C/R2 was shown to be superior to several other monovalent vaccines and was the equal of a bivalent (HVT+SB-1) vaccine [Witter, Avian Dis. 31:752-765 (1987)]. However, the inherent pathogenicity of serotype 1 viruses and the potential of attenuated strains to revert to greater pathogenicity [Witter et al., Avian Pathol. 13:75-92 (1984)] are factors to be considered in the licensing of such products. A clone derived from further passages of the Mdn/75C/R2 strain, designated Md11/75C/R2/23 (or R2/23), was found by Witter et al. [Avian Dis., 35:877-891 (1991)] to possess the highly protective nature of the parent strain without its residual pathogenicity.

Witter also described another MD vaccine derived from 301 B/1, a nonpathogenic serotype 2 field isolate, in U.S. Pat. No. 4,895,718, the contents of which are incorporated by reference herein, strain 301 B/1 possessed superior replicative ability to SB-1, as well as greater protectivity against challenge to viruses.

A recombinant Marek's disease virus, referred to as RM1, having the long terminal repeats of reticuloendotheliosis virus stably integrated into the repeat short (RS) regions of its genome was also described. This strain was generated at the USDA-ARS-ADOL from a pathogenic serotype 1 Marek's disease virus strain JM [Witter et al., 1997, Avian Dis., 41:407-421, and Jones et al., 1996, J. Virology, 70(4): 2460-2467i. However, while the RM1 strain has been shown to provide a level of protection similar or superior to that of CVI988, it has also been associated with residual pathogenicity, causing thymic atrophy in treated birds.

Thus, although existing HVT, SB-1, CVI988, CVI988/C, Md11/75C, Md11/75C/R2 and 301 B/1 all elicit immune responses against certain MD viruses, none of these vaccines protect optimally against all MD challenge viruses in all chickens. Moreover, these vaccines have exhibited reduced efficacy against some of the more recently isolated very virulent strains of MD virus. To avert any large-scale outbreaks of MD in the future, the need exists to develop safer vaccines having improved efficacy against highly virulent strains of MD virus.

SUMMARY OF THE INVENTION

The present invention is based, in part, upon the production and use of vaccines comprising Marek's Disease Viruses (MDV) originally disclosed in application number U.S. Ser. No. 10/623,891 (published as US2005/0019348A1, to Reddy et al.), the contents of which, as well as the application's entire prosecution history, are both herein incorporated by reference in their entirety. Specifically, the present invention stems from the surprising and unexpected finding that the CVRM2 "virus" (MDV strain "CVI988" transformed with a foreign DNA construct; disclosed, for example, in Table 1 of Reddy et al.) was not in fact a clonally distinct, single recombinant attenuated Marek's Disease Virus (MDV). Instead, Applicants determined the CVRM2 was a heterogeneous population of recombinant and parental MDV, and when they isolated and subsequently administered to avians a pure clonal line of CVRM2 (hereinafter referred to as "RN1250"), they obtained safety and efficacy results far exceeding those a skilled person would have expected on reading Reddy et al.

In accordance with this discovery, it is an object of the invention to provide a novel, highly protective vaccine against MD in avians, including chickens. It is also an object of the invention to provide a vaccine which provides greater protection against highly virulent strains of Marek's disease virus than those vaccines presently in commercial use.

It is another object of the invention to improve the viability and productivity of chickens, particularly broilers and layers, and to reduce economic losses in the poultry industry caused by Marek's disease.

These and other embodiments are disclosed or are obvious from, and encompassed by, the following Detailed Description.

BRIEF DESCRIPTION OF THE DRAWINGS

FIG. 3 illustrates PCR-based diagnostic of recombinant MDV; presented are the PCR primers, expected product sizes, and agarose gel image, which indicates the CVRM2 was not clonal, but in fact a dual population of recombinant and parental MDV. Lanes: 1) ladder; 2) negative; 3) Rispens; 4) GA 22; 5) Rismavac; 6) RB1B; 7) RN1250; 8) positive (original mixed population);

DETAILED DESCRIPTION OF THE INVENTION

Definitions

Figure 1:
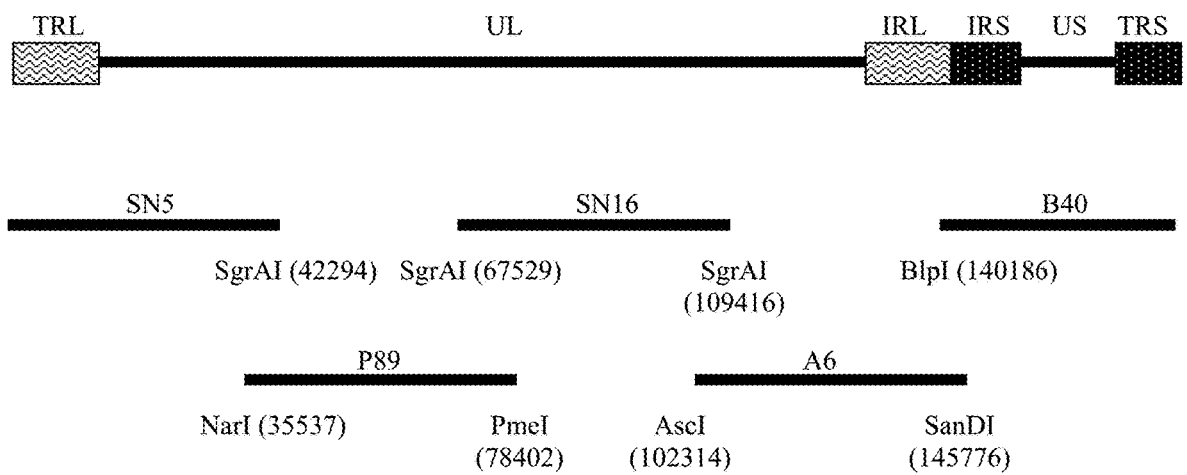
FIG. 1 shows a schematic organization of MDV genome, which contains a unique long (UL) region flanked by inverted repeat (IRS), terminal repeat long (TRL), internal repeat long (IRL), and a unique short region (US), and is flanked by two inverted repeats, internal repeat short (IRS) and terminal repeat short (TRS). Also shown is a schematic representation of the overlapping cosmid clones generated to rescue an infectious virus from a highly virulent strain of MDV.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Cloning. The selection and propagation of (a) genetic material from a single individual, (b) a vector containing one gene or gene fragment, or (c) a single organism containing one such gene or gene fragment.

Cloning vector. A plasmid, virus, retrovirus, bacteriophage, cosmid, artificial chromosome (bacterial or yeast), or nucleic acid sequence which is able to replicate in a host cell, characterized by one or a small number of restriction endonuclease recognition sites at which the sequence may be cut in a predetermined fashion, and which may contain an optional marker suitable for use in the identification. of transformed cells, e.g., tetracycline resistance or ampicillin resistance. A cloning vector may or may not possess the features necessary for it to operate as an expression vector.

Expression. The process undergone by a structural gene to produce a polypeptide. Expression requires transcription of DNA, post-transcriptional modification of the initial RNA transcript, and translation of RNA.

Expression Cassette. A nucleic acid sequence within a vector which is to be transcribed, and a promoter to direct the transcription. The expression cassette may contain one or more unrelated DNA sequences encoding one or more peptides of interest.

Expression Control Sequence. Expression control sequences are DNA sequences involved in any way in the control of transcription or translation and must include a promoter. Suitable expression control sequences and methods of making and using them are well known in the art.

Expression vector. A replicon such as a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Operably Encodes or Associated. Operably encodes or operably associated each refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Promoter. A DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, I.e., occurring naturally to direct the expression of a nucleic acid derived from a gene other than the desired nucleic acid. A promoter may be constitutive or inducible.

Vaccine. A vaccine is defined herein in its broad sense to refer to any type of biological agent in an administrable form capable of stimulating a protective immune response in an animal inoculated with the vaccine.

Embodiments

The present invention provides Recombinant Marek's disease virus (MDV), into which has been inserted via homologous recombination, a long terminal repeat (LTR) derived from a reticuloendotheliosis virus (REV). These recombinants are effective to elicit an immune response in an avian to Marek's disease virus without causing a significant degree of pathogenicity in the avian. As used herein, "without causing a significant degree of pathogenicity" is defined as no gross MD-specific lesions being observable with the naked eye in the inoculated/challenged avian, even in highly susceptible avians. In particular embodiments, the avians are chickens.

Figure 2:
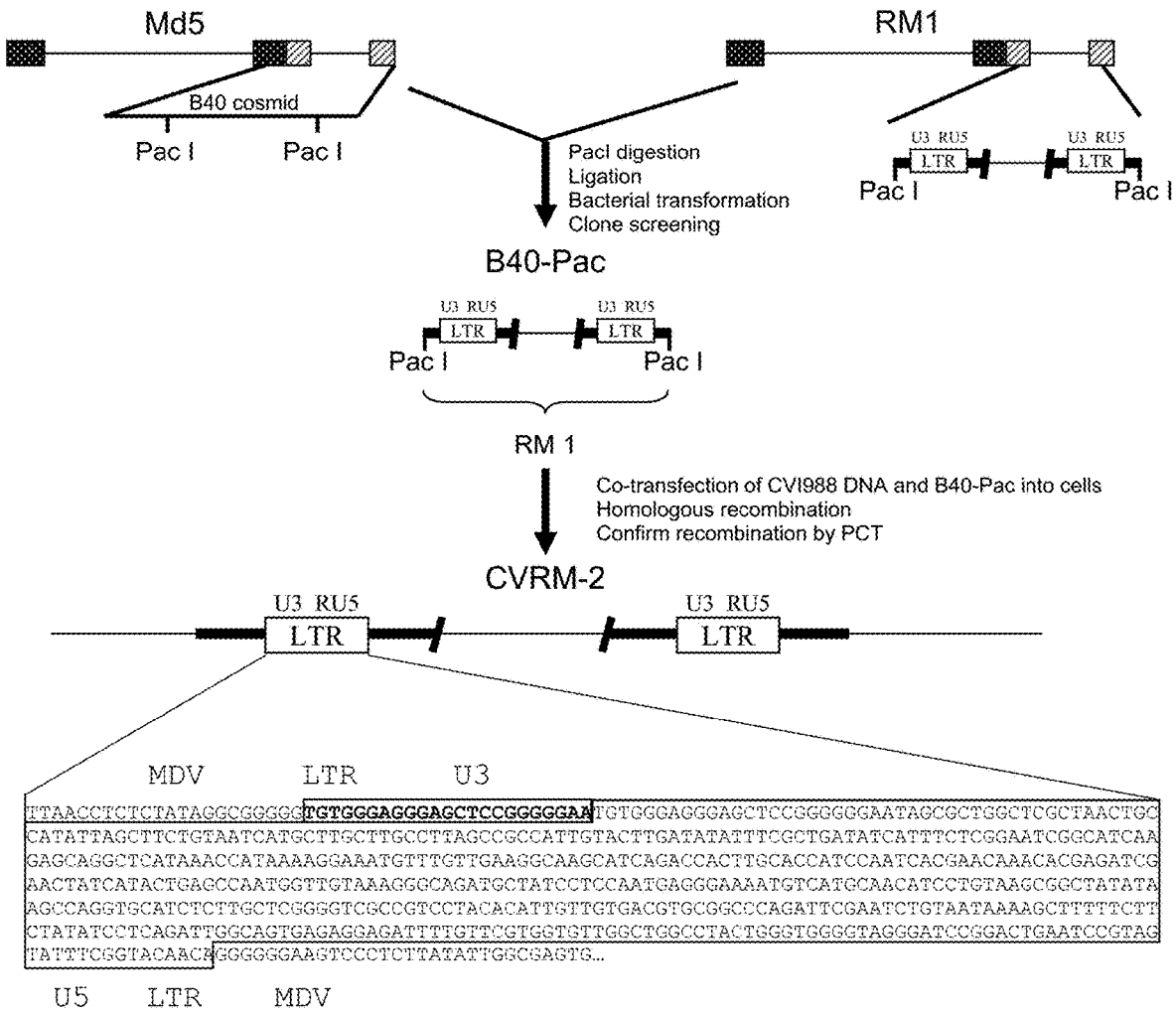
FIG. 2 depicts generation of the B40-Pac cosmid used to generate the CVRM vaccine, and shows SEQ ID NOs: 1 and 2.
Figure 4:
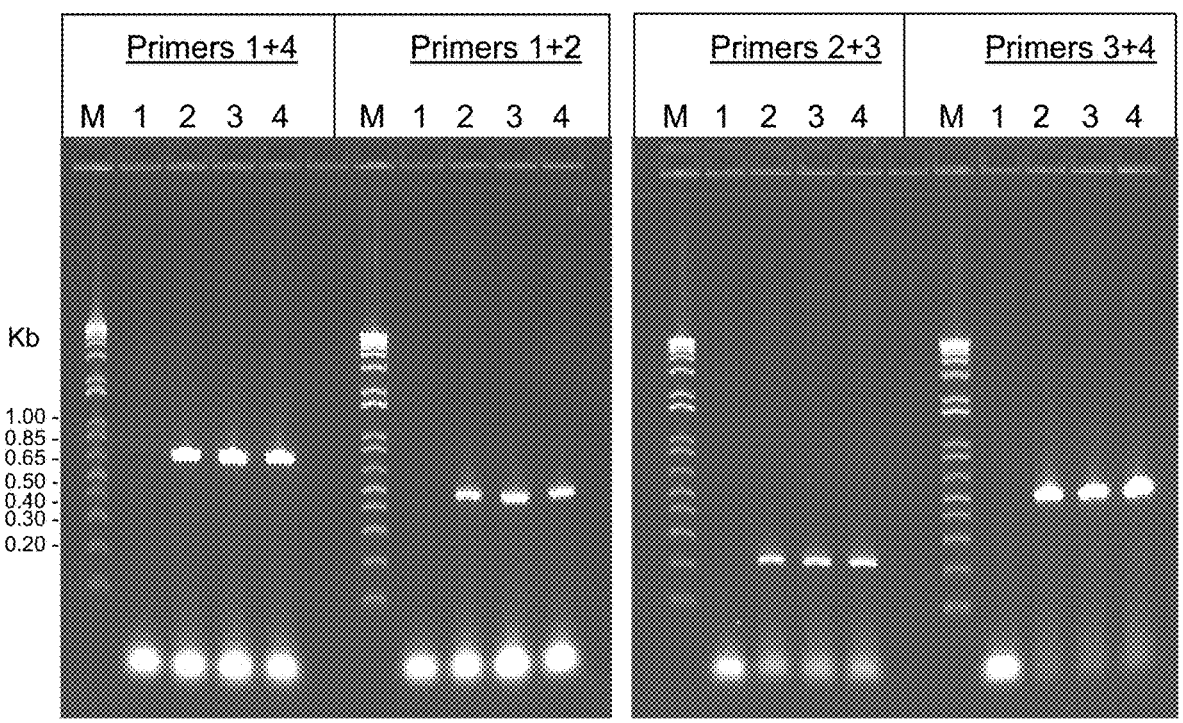
FIG. 4 presents PCR confirmation of RN1250 MSV, RN1250 x+5, and BP5. Lanes: no template (1), RN1250 MSV (2), RN1250 x+5 (3), RN1250 BP5 (4). PCR reactions with all primer pairs resulted in the expected PCR product and banding pattern, thus there was no evidence for presence of the parental Rispens virus among RN1250 MSV, RN1250 x+5, and BP5 isolates.

CVRM-2 was produced by authors of Reddy et al., as described therein, and as summarized in FIGS. 1 and 2 of this disclosure. Upon receipt of the CVRM2 sample, instant Applicants performed careful PCR-based analysis to confirm the identity/integrity of the virus isolate (FIG. 3 presents the agarose gel resolution of the amplified products). Applicants found to their surprise the sample was not a clonal isolate, but was in fact a combined population of recombinant CVRM2 and the parental MDV strain. Applicants then performed the necessary plaque purification to obtain a pure isolate consisting only of CVRM2 (and not the parental MDV Rispens strain). For clarity, the new, clonal isolate is referred to as "RN1250" throughout this disclosure.

The recombinant MDV of this invention may be produced by modification of MDV serotype 1 strain CVI988, or any of its clones or serially passaged strains, which are collectively referred to herein as strains "CVI988/X". Thus, as used herein CVI988/X includes, but is not limited to, the previously described original low-passage strain, CVI988/Rispens (Rispens et al., 1972, Avian Dis., 16:106-125 and 126-138), strain CVI988 clone C (CVI988/C) (De Boer, U.S. Pat. No. 4,673,572, and De Boer et al., 1986, Avian Dis. 30:276-283), and CVI988/C/R6 (De Boer et al., 1988, Advances in Marek's Disease Research, pp. 405-413). The contents of each of the above-mentioned publications/patents are incorporated by reference herein.

In an embodiment, the invention provides for a novel, recombinant, attenuated MDV strain, which is produced replacing a portion of the native CVI988/X sequence with exogenous DNA, which comprises a long terminal repeat (LTR) sequence from a reticuloendotheliosis virus (REV).

In an embodiment, recombination of strain CVI988 was effected using MDV serotype 1 strain RM1 as a source of the exogenous LTRs (RM1 is a recombinant MDV into which REV LTRs had been integrated). As shown in FIG. 2, the REV LTR was excised from the purified RM1 viral DNA by Pac 1 digestion and inserted into a shuttle vector, B40, prepared from a very virulent strain of Marek's disease virus, Md5. The resultant recombinant vector, B40-Pac, was used for insertion of the LTRs into the Marek's disease virus strain CVI988. To generate recombinant MDV with the LTRs, the purified viral DNA of MDV strain CVI988 was co-transfected into chicken or duck embryonic fibroblast (CEF or DEF) cells with Not I-digested recombinant vector. Recombinant viruses having the RM1 LTRs integrated into their genome replicated more quickly than the parental CVI988 strain. Without being bound by theory, it is believed that this increased rate of replication is the result of the insertion of the reticuloendotheliosis virus LTR into the genome of the MDV upstream of the ICP4 gene.

In another embodiment, the MDV CVI988/X may be modified via the addition of isolated reticuloendotheliosis virus LTRs from sources other than the RM1 strain. For instance, the insertion site of the LTR in the RM1 strain of MDV has been shown to be between IRL and IRS of the genome (Jones et al., 1996, Retroviral insertional activation in a herpesvirus: transcriptional activation of US genes by an integrated long terminal repeat in a MDV clone, J. Virology, 70(4):2460-2467). This corresponds approximately to position 152,745 of the Md5 strains of Marek's disease virus. This region is located within a 1,704 base pair long EcoR1 fragment (nucleotides 152, 198-153, 902) of serotype 1 Md5 (Tulman et al., 2000, The genome of a very virulent Marek's disease virus, J. Virology, 74d7):7980-7988). This 1,704 bp EcoR1 fragment can be cloned into a plasmid vector lacking DraIII restriction endonuclease site and used as a transfer vector for introduction of any LTR in to the MDV genome. This EcoRX fragment has a unique DraIII restriction site located 10 bp upstream of the LTR location in RM1. The LTRs can be inserted into the DraIII site of the 1,704 base pair EcoR1 fragment to generate the LTR transfer vector, in order to generate recombinant MDV with LTR insertions, the transfer vector should be linearized with EcoR1, extracted with phenol and chloroform and precipitated with ethanol. Co-transfection of the linearized transfer vector along with DNA from any serotype 1 MDV strain into permissible cells in culture will result in the introduction of LTR sequences into the MDV genome by homologous recombination.

Reddy et al., supra, indicated the resulting recombinant virus (i.e. MDV with a reticuloendotheliosis LTR) should "grow more rapidly than its corresponding parental MDV strain, and thus there is no need for plaque purification". However, in view of Applicants' unexpected finding that the CVRM-2 sample was in fact a combination of recombinant MDV plus its corresponding parental MDV, the skilled person is advised strongly to plaque purify all recombinant MDV envisioned by the instant disclosure. This is particularly important because a skilled person could be mistakenly encouraged to discard a potentially useful recombinant MDV after obtaining results indicating immunization with the virus fails to provide sufficient protection against a subsequent virulent MDV challenge (please see Table 1 of Reddy et al., where CVRM-2 appears to provide less than 80% protection).

In another embodiment, recombinant MDV having the RETV LTRs may be prepared from any MDV, including other CVI988/X strains, using the deposited CVRM-2, provided the CVRM-2 is plaque purified to ensure the virus is RN1250, and not a combination of RN1250 and the parental MDV strain.

A variety of REV LTRs are suitable for use herein. Numerous suitable reticuloendotheliosis viral LTRs have been isolated and described, and include but are not limited to those described by Kost et al. (1993, Retrovirus insertion into herpesvirus: characterization of a Marek's disease virus harboring a solo LTR, Virology, 192:161-169), Ridgway (1992, REV LTR elements are efficient promoters in cells of various species and tissue origin, including human lymphoid cells, Gene, 121:213-218), Boerkoel and Kung [1992, Transcriptional interaction between retroviral long terminal repeats (LTRs): mechanism of 5' LTR suppression and 3' LTR promoter activation of c-myc in avian B-cell lymphomas, J. Virol., 66:4814-4823], Hippenmeyer and Krivi (1991, Gene expression from heterologous promoters in a replication-defective avian retrovirus vector in quail cells, Poult. Sci., 70:982-92), Ridgway et al. (1989, Transient expression analysis of the reticuloendotheliosis virus long terminal repeat element, Nucleic Acids Res., 17:3199-3215), Embretson and Temin (1987, Transcription from a spleen necrosis virus 5' long terminal repeat is suppressed in mouse cells, J. Virol., 61:3454-3462), Notani and Sauerbier (1987, Sequence instability in the long terminal repeats of avian spleen necrosis virus and reticuloendotheliosis virus, J. Mol. Evol., 25:241-247), Robinson and Gagnon (1986, Patterns of proviral insertion and deletion in avian leukosis virus-induced lymphomas, J. Virol., 57:28-36), and Ridgway et al., (1985, In vitro transcription analysis of the viral promoter involved in c-myc activation in chicken B lymphomas: detection and mapping of two RNA initiation sites within the reticuloendotheliosis virus long terminal repeat, J. Virol., 54:161-170). The contents of each of the publications referred to above are incorporated by reference herein, in addition, numerous LTR sequences are available in GenBank and other genomic databases and can be synthesized by PCR using LTR specific primers. The PCR amplified sequences can then be inserted in any of the two transfer vectors described as indicated above.

The REV LTR nucleic acid sequences disclosed herein, or their biologically functional equivalents, can be used in accordance with the present invention. The phrase "biologically functional equivalents" as used herein, denotes nucleic acid sequences exhibiting the same or similar biological activity/immunoprotective activity as the above-mentioned reticuloendotheliosis viral LTR nucleic acid sequences (i.e., when introduced into the CVI988 MDV host in a functionally operable manner they elicit a protective immune response without causing a significant degree of pathogenicity in the chicken).

For example, the nucleic acid sequences described herein can be altered by base substitutions, insertions, additions, or deletions to produce biologically functionally equivalent nucleic acids that retain promoter or enhancer activity.

The variants of the genomic DNAs or cDNAs (if obtained by RT-PCR from RNA), contemplated herein should possess more than 75% homology, preferably more than 85% homology, and most preferably more than 95% homology, to the naturally occurring REV LTRs discussed herein.

The vaccine of the recombinant Marek's disease virus of the invention may be prepared as a cell-free preparation, or in the preferred embodiment, as a cell-associated preparation. A cell-associated vaccine can be prepared directly from In vitro culture of the live viral agents in a suitable growth medium, such as chicken embryo fibroblasts as described by Witter (U.S. Pat. No. 4,895,718, the contents of which are incorporated by reference herein). Alternatively, to prepare cell-free virus inocula, cells from infected host tissue or cell culture are sonicated or otherwise disrupted as previously described. The cellular debris is removed by centrifugation and the centrifugate recovered as the inoculum. Moreover, while the preferred vaccine is a viable virus, it is also envisioned that the vaccine may be prepared from the killed virus or from immunogenic components separated from the virus, although such processing would incur significantly greater costs. For example, a subunit vaccine can be prepared by separating from the killed virus one or more purified viral proteins identified as having immunogenic properties.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of Marek's disease virus, immunity is considered as having been induced in a population of chickens when the level of protection for the population is significantly higher than that of an unvaccinated control group (measured at a confidence level of at least 80%, preferably measured at a confidence level of 95%). One measure of the level of protection is the protective index (Pi), which is calculated as the incidence of MD in unvaccinated, MDV challenged controls minus the incidence of MD in vaccinated, MDV challenged groups, and the difference divided by the percent of Marek's disease in unvaccinated, MDV challenged controls, with the result multiplied by 100.

Typically, the vaccine will contain at least about 200 PFU (plaque-forming units) of the virus, and preferably between about 2000 and 5000 PFU. The vaccine can be effectively administered any time after the chicken attains immunocompetence, which is at about the 18th day of incubation (3 days prehatch); but it is normally administered by inoculation within 24-48 hours after hatching. Alternatively, the recombinant viral DNA may be administered as a DNA vaccine as described by Tischer et al. (2002, J. Gen. Virology, 83:2367-2376, the contents of which are incorporated by reference herein).

Appropriate adjuvants as known in the art may also be included in the vaccine formulation. In many cases, the vaccinal efficacy can be enhanced by combining the recombinant Marek's disease viruses of the invention with other viral agents into bivalent or polyvalent vaccines.

In another embodiment, the pharmaceutically or veterinarily acceptable carrier, excipient, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, or vehicle may be an oil-in-water emulsion.

Methods of Use and Article of Manufacture

The present invention includes the following method embodiments. In an embodiment, a method of vaccinating an avian comprising administering a composition comprising a Marek's Disease virus (MDV).

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions is generally between about 0.1 to about 2.0 ml, between about 0.1 to about 1.0 ml, and between about 0.5 ml to about 1.0 ml.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a dog, ferret or seal.

Another embodiment of the invention is a kit for performing a method of eliciting or inducing an immunological or protective response against MDV in an animal comprising a recombinant MDV immunological composition or vaccine and instructions for performing the method of delivery in an effective amount for eliciting an immune response in the animal.

In an embodiment, the subject matter disclosed herein is directed to a kit for performing a method of eliciting or inducing an immune response which may comprise any one of the recombinant MDV compositions or vaccines and instructions for performing the method.

Other cytokines that may be used in the present invention include, but are not limited to, granulocyte colony stimulating factor (G-CSF), granulocyte/macrophage colony stimulating factor (GM-CSF), interferon α (IFNγ), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to avians).

The invention will now be further described by way of the following non-limiting examples.

Example 1—Efficacy of Marek's Disease Virus (MDV), SR-1 Strains, CVRM-2 RN1250 and RMI CN32399, and Rispens CN32553

A critical aspect of the instant invention is that after having completed the study outlined in this Example, inventors later determined the CVRM-2 MDV was not a clonal recombinant MDV, but in fact was a mixed population of RN1250 recombinant MDV and parental Rispens MDV. Thus, now that inventors have produced a stable, clonal RN1250 MDV, which virus' strong efficacy as a vaccine is demonstrated in later Examples, a skilled person will not be surprised by the broad (and unacceptable) range of protection (37-86%) apparently provided by the CVRM-2 MDV in this preliminary study.

Objective. To evaluate and compare the efficacy of three experimental MDV SR-1 and Rispens strains to a commercial vaccine product (Rismavac®-Intervet, Inc.) in SPF Chickens using an early challenge with MDV T. King.

Materials/Methods. One hundred fifty one-day-old SPF chicks (SPAFAS flock W-42) were randomly assigned to five different groups of thirty birds each (Groups 1-5). Each treatment group was then randomly assigned to isolation units. The chicks in Group 1 used as the non-vaccinated, challenged controls were placed into negative pressure isolation units first, fifteen birds per unit. Each remaining group (Groups 2-5) were then subcutaneously (SQ) vaccinated with 0.2 ml per bird with either Intervet Rispens Rismavac®; MDV SR-1 RMI CN32399 $P_4$; MDV SR-1 CVRM-2 RN1250 $P_4$; or MDV Rispens CN32553 $P_4$. The SQ vaccinated birds in Groups 2-5 were also placed in negative pressure isolation units, 15 birds per unit. Four days later on Study Day 4, the birds in Groups 1-5 were challenged individually with MDV T. King, diluted 1:500 (protocol 02-085 2 Jan. 2003). Birds were challenged intraperitoneally (IP), with 0.2 ml per bird. Birds were observed for 49 days post-challenge. Any bird that died prior to Study Day 53 was necropsied and examined for MDV lesions. On Day 53, all remaining birds were terminated, necropsied and examined for MDV lesions.

Results. The experimental MDV SR-1 and Rispens strains provided protection rates of 37-86% against the early MDV T. King challenge. Intervet's Rismavac® provided 83% protection. The challenge was validated with the non-vaccinated, challenged control birds showing MD incidence of 97%.

Example 2—Efficacy of MDV, SR-1, RN1250 Vaccine in Commercial Broilers Using a Shedder Challenge Model Materials & Methods: Seventy-six (76) one-day-old commercial broilers obtained from Harrison poultry flock 1-1 were randomized into three different colony houses and four different groups as follows: Group 1: 13 birds; Group 2: 13 birds; Group 3: 25 birds; and Group 4: 25 birds (one house was split into two sides in order to create pen one and pen two). After randomizing, the birds were banded in the nape of the neck for identification and then were inoculated with 0.2 ml per bird intraperitoneally (IP) with vvMDV T. King challenge, diluted 1:500. After challenging, the birds were placed into their respective colony house with 25-26 birds per house. These birds remained in the colony houses for 14 days prior to the placement of MDV vaccinated and non-vaccinated, contact control birds. Fourteen days after placement of the shedder birds, 304 one-day-old commercial broilers were randomized as follows: two groups with 75 birds each (Groups 3 and 4) and two groups with 38 and 40 birds each (Groups 1 and 2), to serve as vaccinates; in addition, two groups of 25 birds and two with 13 birds were used to serve as non-vaccinated, contact control birds for Groups 1-4 (Group 1: 13 birds; Group 2: 13 birds; Group 3: 25 birds; and Group 4: 25 birds). These contact control birds were banded in the nape of the neck for identification and placed in the colony houses. The vaccinates were inoculated by the subcutaneous route (SQ) route (0.2 ml per bird) as follows: Group 1 was vaccinated with RN1250 pre MSV, P6 (isolate I); Group 2 was vaccinated with RN1250 pre MSV, P7 (isolate U); Group 3 was vaccinated with RN1250 pre MSV, P7 (isolate F); and Group 4 was vaccinated with Rismavac® serial 02760010, exp. 15 Apr. 2012. After the inoculations, the vaccinates were placed in the same colony houses where the non-vaccinated, contact control birds and shedders were placed previously. An additional fifty (50) non-inoculated one-day-old commercial broilers were housed in isolation units, and were kept for 49 days in order to serve as a second group of contact controls at a later day.

All the vaccinated birds were banded in the nape of the neck eight days later with color coded, numbered bands. The shedders remained in the colony houses for fifty days, and then all the survivors were terminated and necropsied.

Clinical disease and mortality were monitored daily for 49 days post-vaccination. The spleens from any contact control bird that died were collected for virus isolation. On study day 53, the forty non-inoculated commercial broilers that were housed in isolation units, in order to serve as the second group of contact controls, were placed in the colony houses, Groups 1-4, according to a randomization schedule, 10 birds per group. These birds were banded with numbered bands before placement for identification. The spleens from these birds were also collected for virus isolation in the event that mortality occurred. The remaining vaccinates and the initial non-vaccinated, contact control birds were terminated and necropsied at the of the 49 day observation period on study day 63. Spleens and at least two feather follicles per bird were collected from 10 contact controls for virus isolation. The sampled birds were determined by a randomization schedule. On study day 83, the remaining contact control birds that were added to the groups on study day 53 (second group), were terminated. Spleens and at least two feather follicles per bird were collected from these contact control birds for virus isolation.

TABLE 1

Number of birds surviving to five day of age

| Regime | Group | Name | # survivors to 5 days of age/total # birds |
|---|---|---|---|
| Vaccinated | 1 | RN1250 pre MSV (I) | 38/38 |
| Vaccinated | 2 | RN1250 pre MSV (U) | 40/40 |
| Vaccinated | 3 | RN1250 pre MSV (F) | 73/75 |
| Vaccinated | 4 | Rismavac ® | 73/75 |
| Contact control | 1 | RN1250 pre MSV (I) | 12/13 |
| Contact control | 2 | RN1250 pre MSV (U) | 13/13 |
| Contact control | 3 | RN1250 pre MSV (F) | 22/25 |
| Contact control | 4 | Rismavac ® | 23/25 |

TABLE 2

Protective indexes against the vvMDV T. King challenge

| Regime | Gp | Name | # infected/total # birds | Percent Infected | Protective Index[5] |
|---|---|---|---|---|---|
| Vaccinated | 1 | RN1250 pre MSV (I)[1] | 2/38 | 5.26% | 87.4 (81.2)[6] |
| Vaccinated | 2 | RN1250 pre MSV (U)[2] | 6/40 | 15.0% | 2.6 (46.4)[6] |
| Vaccinated | 3 | RN1250 pre MSV (F)[3] | 6/73 | 8.22% | 84.9 |
| Vaccinated | 4 | Rismavac ®[4] | 15/73 | 20.5% | 63.7 |
| Shedders | 1 | RN1250 pre MSV (I) | 9/12 | 75.0% | N/A |
| Shedders | 2 | RN1250 pre MSV (U) | 11/12 | 91.7% | N/A |
| Shedders | 3 | RN1250 pre MSV (F) | 20/25 | 80.0% | N/A |
| Shedders | 4 | Rismavac ® | 22/24 | 91.7% | N/A |
| Contact control | 1 | RN1250 pre MSV (I) | 5/12 | 41.7% | N/A |
| Contact control | 2 | RN1250 pre MSV (U) | 2/13 | 15.4% | N/A |
| Contact control | 3 | RN1250 pre MSV (F) | 12/22 | 54.5% | N/A |
| Contact control | 4 | Rismavac ® | 13/23 | 56.5% | N/A |
| 2$^{nd}$ controls | 1 | RN1250 pre MSV (I) | 9/10 | 90.0% | N/A |
| 2$^{nd}$ controls | 2 | RN1250 pre MSV (U) | 8/10 | 80.0% | N/A |
| 2$^{nd}$ controls | 3 | RN1250 pre MSV (F) | 9/10 | 90.0% | N/A |
| 2$^{nd}$ controls | 4 | Rismavac ® | 8/10 | 80.0% | N/A |

[1]RN1250 (I) vaccine titer: 3600 pfu/0.2 ml.
[2]RN1250 (U) vaccine titer: 3144 pfu/0.2 ml.
[3]RN1250 (F) vaccine titer: 3710 pfu/0.2 ml.
[4]Rismavac ® vaccine titer: 2328 pfu/0.2 ml.
[5]Protective index: Percentage of non-vaccinated contacts with MD lesions (challenge controls) − Percentage of vaccinated chickens with MD lesions/Percentage of non-vaccinated contacts with MD lesions (challenge controls).
[6]Protective index considering the percentage of non-vaccinated contact controls with MD lesions in Colony House 10, Groups 1 and 2, as only one group (28% or 7/25).

Conclusion. The Marek's Disease Vaccine, Serotype 1, RN1250 Vaccine, pre MSV (I) and (F), were more efficacious than Intervet's Rismavac® in commercial broilers using MDV T. King in a shedder challenge model.

Example 3—Safety MDV RN1250 (X+5) in SPF One-Day-Old Chicks

Two hundred-fifty, one-day-old, SPF chickens were randomly assigned to five treatment groups, 50 chicks per group, as well as, randomly assigned to the negative pressure isolation units used for housing. One hundred chicks were designated as vaccinates and were identified as Groups 1 and 2. One hundred chicks were designated as the sham-vaccinated, contact controls of Groups 1 and 2 (Groups 4 and 5, respectively); the remaining sham-vaccinated chicks (50) were identified as Group 3 to serve as the negative controls. After randomizing, the sham-vaccinated, contact controls and sham-vaccinated, negative controls were wing-banded with numbered bands for identification and were placed into their respective units (7-10 birds per unit). The sham-vaccinated birds were inoculated with Marek's Disease diluent, 0.2 ml per bird. The chicks designated as vaccinates were subcutaneously (SQ) inoculated with either: RN1250 (X+5) (Group 1) or Rismavac® (Group 2), 0.2 ml per bird (~5000-6500 plaque-forming units (pfu) per dose). After the inoculations, the vaccinates were placed into their assigned units (7-10 birds per unit) with their sham-vaccinated, contact controls which had been previously housed, for a total of 15 to 20 chicks per unit.

TABLE 3

Study Design

| GROUP | VACCINE | VACCINATION* ROUTE | NUMBER of BIRDS |
|---|---|---|---|
| 1 | MDV SR-1 RN1250 | SQ | 50 |
| 2 | MDV SR-1 Rismavac ® | SQ | 50 |
| 3 | Sham-vaccinated (Negative Controls) | SQ | 50 |
| 4 | Sham-vaccinated Contact Controls for MDV SR-1 RN1250 vaccinated birds | SQ | 50 |
| 5 | Sham-vaccinated Contact Controls for MDV SR-1 Rismavac ® vaccinated birds | SQ | 50 |

On Study Day 7, organ samples (bursa, thymus and spleen) from five birds belonging to each group, Groups 1-5, were chosen for harvesting and fixed in 10% buffered formalin for histopathology. The birds, 2-3 birds per unit, were selected according to a randomization schedule. On Study Day 14, body weights and organ weights (bursa, thymus and spleen) of 15 birds from each group, Groups 1-5, were collected. Organ samples (bursa, thymus and spleen) from five birds in each group (Groups 1-5) were harvested and fixed in 10% buffered formalin. Two to three birds per unit were used for the weighing and organ harvest. The birds were selected according to a randomization schedule. The procedure described on Study Day 14, was repeated on Day 28, and on Day 49 with the remaining birds.

Results. Organs Atrophy RN1250. The bursa ratios of birds vaccinated with MDV SR-1 RN1250 vaccine and the ratios of the sham-vaccinated, contacts controls were not significantly different from that of the sham-vaccinated, negative control birds, except that on Day 28, the bursa ratio of the contact controls for MDVSR-1 RN1250 was significantly higher than that of the negative controls ($p \geq 0.0111$). The thymus ratios of birds vaccinated with MDVSR-1 RN1250 vaccine and the ratios of the sham-vaccinated, contacts controls were not significantly different from that of the sham-vaccinated, negative control birds ($p \geq 0.7265$). Finally, the spleen ratios of birds vaccinated with MDVSR-1 RN1250 vaccine and the ratios of the sham-vaccinated, contacts controls were not significantly different from that of the sham-vaccinated, negative control birds ($p \geq 0.5286$).

Organs Atrophy Rismavac®

The bursa ratios of birds vaccinated with MDVSR-1 Rismavac®-vaccine and the ratios of the sham-vaccinated, contacts controls were not significantly different from that of the sham-vaccinated, negative control birds ($p \geq 0.0581$). The thymus ratios of birds vaccinated with MDVSR-1 Rismavac®-vaccine and the ratios of the sham-vaccinated, contacts controls were not significantly different from that of the sham-vaccinated, negative control birds ($p \geq 0.4004$). The spleen ratio of birds vaccinated with MDVSR-1 Rismavac®-vaccine was significantly greater than the spleen ratio of the sham-vaccinated, negative controls on Day 14 with p-value=0.0141; and the spleen ratios of birds of sham-vaccinated contract controls was significantly greater than that of the sham-vaccinated, negative controls on Day 28 with p-value<0.0001. The ratios were not significantly different on any other days ($p \geq 0.5558$) Histological Examination Results from the histological examination did not shown evidence of atrophy in the bursa, thymus or spleen of the birds inoculated with the Marek's Disease SR-1 RN1250 or Rismavac®.

Conclusion. Under the conditions of this trial the MDV SR-1, RN1250, X+5, was safe when administered SQ, as evaluated by thymic, bursa and/or spleen atrophy.

Example 4—Dissemination of MDV, SR-1, RN1250 in SPF One-Day-Old Chicks

Objective. To evaluate the dissemination of the MDV, SR-1, RN1250 experimental vaccine (X+5) in one-day-old specific-pathogen-free (SPF) chickens when administered SQ and whether it would shed and spread to non-vaccinated contacts.

Materials & Methods. One hundred twenty (120) one-day-old SPF chickens were randomized into three different treatment groups and six units with each unit containing 15 vaccinates and five contacts. The birds randomized as contacts were banded in the nape of the neck with colored numbered bands per the randomization schedule and then placed into their respective units. The birds randomized as vaccinates were vaccinated with either MDV RN1250 X+5 or Rispens. The experimental and commercial vaccines were diluted in Marek's diluent to yield approximately 100,000 pfu per dose (approximately 17× the expected field dose) administered by the SQ route. After vaccination, the birds were placed into their respective units along with the contacts that were previously placed. The vaccinated birds were banded at eight days of age in the nape of the neck with colored numbered bands according to a randomization schedule. Personnel involved with clinical assessments during the study were not present for the banding of the contacts or vaccinates nor did they perform any clinical observations during this time period in order to maintain blinding.

TABLE 4

Study Groups

| GP | VACCINE | VACCINATION ROUTE/ VOLUME | NUMBER of BIRDS* Vaccinated | Non-vaccinated contacts |
|---|---|---|---|---|
| 1 | MDV SR-1 RN1250 | SQ/ 0.2 ml per bird | 30 | 10 |
| 2 | MDV SR-1 Rispens vaccine | SQ/ 0.2 ml per bird | 30 | 10 |
| 3 | Sham-vaccinated Negative Controls | SQ/ 0.2 ml per bird | 30 | 10 |

At two weeks post-vaccination, tracheal and cloacal swabs were taken for virus recovery from all vaccinated birds. The swabs were pooled by group, with five tracheal or cloacal swabs per swab tube containing 5 ml of SPGA stabilizer. Primary feather follicles were collected for virus recovery from two vaccinated birds in each group, collecting two to three feather samples per bird. The two birds per group for feather follicle sampling were selected according to a randomization schedule and were kept alive after sampling. All samples were taken to Merial Select's analytical department for processing. The same sampling procedure was repeated two times at seven day intervals.

On study day 21, in addition to tracheal and cloacal swab sampling and feather follicle sampling, five vaccinated and non-vaccinated contacts per group (selected according to a randomization schedule) were terminated and necropsied, with spleens were individually harvested. Virus isolation was attempted only on the spleens harvested from the non-vaccinated contacts (vaccinated birds were harvested to maintain blinding). On the last day of the study (Day 49), all the remaining birds were euthanized and necropsied and the study was terminated. Spleens from the remaining five vaccinated and non-vaccinated contacts per group were individually harvested. Virus isolation was only attempted on the spleens harvested from the non-vaccinated contacts (vaccinated birds were harvested to maintain blinding).

Results. Group one MDV SR-1 RN1250 X+5 arithmetic mean titer (AMT) was 94,160 pfu/0.2 ml dose. Group two MDV SR-1 Rispens was 51,800 pfu/0.2 ml dose. All tracheal and cloacal swabs were negative for virus recovery.

Group 1 MDV SR-1 RN1250: All of the samples tested for this group were negative for virus recovery from feather follicles.

Group 2 MDV SR-1 Rispens: On day 21, feather follicles from both of the birds sampled were positive for Marek's disease cytopathic effect (MD CPE). On days 14 and 28 feather follicles from all birds sampled were negative.

Group 3 Sham-vaccinated negative controls: All of the feather follicle samples tested were negative for virus recovery from feather.

There was no virus recovered from any of the spleens harvested from the contacts birds at Days 21 and 49. The samples from day 49 were initially contaminated but were tested again using PCR and were all negative. Frozen buffy coat material from these same samples was also re-plated and all of these samples were confirmed negative.

Conclusion. Under the conditions of this study, birds vaccinated SQ with the MDV, SR-1, RN1250 experimental vaccine showed similar dissemination patterns to birds vaccinated SQ with the commercially available MDV, SR-1 Rispens vaccine. There was no recovery of virus or evidence of clinical disease in non-vaccinated birds that were in contact with birds vaccinated with the MDV RN1250 experimental vaccine.

Example 5—Evaluation of the Efficacy of MDV, S1, RN1250 Vaccine (X+5) Administered to Day-Old Chicks Against vvMDV, RB1B Virus Materials & Methods. Two hundred eighty (280) one-day-old SPF chicks were randomized into eight different groups and 24 different isolation units according to a randomization schedule (11-12 birds per unit; 35 birds per treatment). After the randomization, the birds in Groups 6 and 7, the sham-vaccinated, challenged and sham-vaccinated/sham challenged negative controls, were sham vaccinated with Marek's vaccine diluent and were placed into their designated units according to the randomization schedule. The remaining birds were then vaccinated with MDV SR-1 RN1250, (deposited with the American Type Culture Collection (ATCC) in Manassas, Va., USA, under ATCC Accession Number PTA-122066 on Mar. 24, 2015, under the terms of the Budapest Treaty) at either 287, 578, 736, 1085, or 1392 plaque forming units (pfu's) per bird dose, or with MDV SR-3 HVT, 1728 pfu's per bird dose. The birds were vaccinated subcutaneously (SQ) with 0.2 ml per chick. After the vaccinations, each vaccinated group was placed into its designated unit according to the randomization schedule. On study day 4, the birds in Group 7 were sham challenged with Marek's vaccine diluent and Groups 1-6 and 8 were challenged with vvMDV RB1B, by the intraperitoneal (IP) route, 0.2 ml per bird. The birds were observed daily for 45 days post-challenge for any unfavorable reactions to the challenge, particularly death or depression. On study day 49, the birds were terminated and necropsied to examine for gross lesions associated with Marek's disease.

Results. The prevented fraction rates against the vvMDV RB1B challenge in Groups 1-5 had a range of 0.84 to 0.94. The prevented fraction in Group 8, the HVT vaccinated group, was 0.73. The incidence of MDV in the sham vaccinated, challenge control Group 6 was 91.2%. The birds in Group 7, the sham vaccinated, sham challenged negative controls, remained free of MDV lesions throughout the study.

Conclusion. The MDV vaccine, Serotype-1, Live Virus, RN1250 Experimental Vaccine (X+5) administered subcutaneously (SQ) to day-old SPF chickens was efficacious at 287 plaque forming units per dose using the RB1B virus as the challenge.

TABLE 5

Dose Response Efficacy Summary

| Gp | Gp | Group Name | Actual dose | # infected/total # of birds | % Protected | % infect. |
|---|---|---|---|---|---|---|
| 1 | B | MDV RN1250 (X + 5) vaccine 250 pfu | 287.2 pfu/0.2 ml (AMT) | 5/34 | 85.3% | 14.7% |
| 2 | H | MDV RN1250 (X + 5) vaccine 500 pfu | 578.4 pfu/0.2 ml (AMT) | 4/34 | 88.2% | 11.8% |
| 3 | C | MDV RN1250 (X + 5) vaccine 750 pfu | 736 pfu/0.2 ml (AMT) | 2/34 | 94.1% | 5.9% |

TABLE 5-continued

Dose Response Efficacy Summary

| Gp | Gp | Group Name | Actual dose | # infected/total # of birds | % Protected | % infect. |
|---|---|---|---|---|---|---|
| 4 | A | MDV RN1250 (X + 5) vaccine 1000 pfu | 1084.8 pfu/0.2 ml (AMT) | 3/35 | 91.4% | 8.6% |
| 5 | D | MDV RN1250 (X + 5) vaccine 1500 pfu | 1392 pfu/0.2 ml (AMT) | 4/34 | 88.2% | 11.8% |
| 6 | E | Sham vaccinated/Challenge Controls | | 31/34 | N/A (8.8%*) | 91.2% |
| 7 | G | Sham vaccinated/Sham Challenge Negative Controls | | 0/35 | N/A | 0.0% |
| 8 | F | MDV HVT Release titer | 1725 pfu/0.2 ml (AMT) | 8/33 | 75.8% | 24.2% |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting a protective immune response against Marek's Disease virus (MDV) in an avian, comprising:

administering to the avian a vaccine, said vaccine comprising a veterinarily or pharmaceutically acceptable carrier or diluent and an effective immunization dosage of a MDV viral agent stably transformed with a foreign DNA construct, comprising a long terminal repeat (LTR) sequence of a reticuloendotheliosis virus, wherein the MDV viral agent is a clonal virus, and not a mixed population of parental and recombinant virus, wherein the MDV viral agent is a CVI988/X MDV SR-1 RN1250 deposited at ATCC under the accession number PTA-122066 and contains at least 200 plaque forming units per dose per avian, and wherein the vaccinated avian has a prevented fraction rate of 0.84 or greater when challenged with vvMDV RB1B virus.

2. The method of claim 1, wherein the avian is a chicken.

3. The method of claim 1, wherein the vaccine does not cause a significant degree of pathogenicity in the avian when administered.

4. A vaccine for eliciting a protective immune response against MDV in an avian, comprising:

a veterinarily or pharmaceutically acceptable carrier or diluent for subcutaneous administration and an effective immunization dosage of a MDV viral agent stably transformed with a foreign DNA construct, comprising a long terminal repeat (LTR) sequence of a reticuloendotheliosis virus, wherein the viral agent is a clonal virus, and not a mixed population of parental and recombinant virus, wherein the MDV viral agent is a CVI988/X MDV SR-1 RN1250 deposited at ATCC under the accession number PTA-122066 wherein the MDV viral agent in the vaccine is present in an amount of at least 200 pfu per dose per avian, and wherein an avian vaccinated with the vaccine has a prevented fraction rate of 0.84 or greater when challenged with vvMDV RB1B virus.

5. The vaccine of claim 4, in a dosage form having a volume between 0.1 mL to 2.0 mL.

6. The method of claim 1, wherein the avian is administered between 0.1 mL to 2.0 mL of the vaccine.

7. The method of claim 1 wherein the LTR has the sequence of SEQ ID NO:2 and the LTR sequence comprises a Pac I excised DNA segment from an MDV having all the identifying characteristics of the strain deposited at ATCC under accession number PTA-4945 and wherein the LTR sequence is inserted 5' of the ICP4 gene of the MDV.

8. The vaccine of claim 4, wherein the LTR has the sequence of SEQ ID NO:2 and the LTR sequence comprises a Pac I excised DNA segment from an MDV having all the identifying characteristics of the strain deposited at ATCC under accession number PTA-4945 and wherein the LTR sequence is inserted 5' of the ICP4 gene of the MDV.

* * * * *

SEQUENCE LISTING

<160> NUMBER OF SEQ ID NOS: 2

<210> SEQ ID NO 1
<211> LENGTH: 585
<212> TYPE: DNA
<213> ORGANISM: Artificial Sequence
<220> FEATURE:
<223> OTHER INFORMATION: Genbak S82226.1 Recombinant MDV Strain RM1
      intervening rpt

<400> SEQUENCE: 1

```
ttaacctctc tataggcggg ggtgtgggag ggagctccgg gggaatgtgg gagggagctc      60
cggggggaat agcgctggct cgctaactgc catattagct tctgtaatca tgcttgcttg     120
ccttagccgc cattgtactt gatatatttc gctgatatca tttctcggaa tcggcatcaa     180
gagcaggctc ataaaccata aaaggaaatg tttgttgaag gcaagcatca gaccacttgc     240
accatccaat cacgaacaaa cacgagatcg aactatcata ctgagccaat ggttgtaaag     300
ggcagatgct atcctccaat gagggaaaat gtcatgcaac atcctgtaag cggctatata     360
agccaggtgc atctcttgct cggggtcgcc gtcctacaca ttgttgtgac gtgcggccca     420
gattcgaatc tgtaataaaa gcttttttctt ctatatcctc agattggcag tgagaggaga     480
ttttgttcgt ggtgttggct ggcctactgg gtggggtagg gatccggact gaatccgtag     540
tatttcggta caacaggggg gaagtccctc ttatattggc gagtg                     585
```

<210> SEQ ID NO 2
<211> LENGTH: 533
<212> TYPE: DNA
<213> ORGANISM: Artificial Sequence
<220> FEATURE:
<223> OTHER INFORMATION: Long Terminal Repeat from Reticuloendothelial
      Virus

<400> SEQUENCE: 2

```
tgtgggaggg agctccgggg gaatgtggga gggagctccg ggggaatag cgctggctcg      60 ctaactgcca tattagcttc tgtaatcatg cttgcttgcc ttagccgcca ttgtacttga     120
tatatttcgc tgatatcatt tctcggaatc ggcatcaaga gcaggctcat aaaccataaa     180
aggaaatgtt tgttgaaggc aagcatcaga ccacttgcac catccaatca cgaacaaaca     240
```

```
cgagatcgaa ctatcatact gagccaatgg ttgtaaaggg cagatgctat cctccaatga    300
gggaaaatgt catgcaacat cctgtaagcg gctatataag ccaggtgcat ctcttgctcg    360
gggtcgccgt cctacacatt gttgtgacgt gcggcccaga ttcgaatctg taataaaagc    420
tttttcttct atatcctcag attggcagtg agaggagatt ttgttcgtgg tgttggctgg    480
cctactgggt ggggtaggga tccggactga atccgtagta tttcggtaca aca           533
```